United States Patent
Hata et al.

(10) Patent No.: US 8,399,694 B2
(45) Date of Patent: Mar. 19, 2013

(54) PROCESS FOR PRODUCING HIGHLY PURIFIED ORANGE ROUGHY OIL

(75) Inventors: Kazuhiko Hata, Tokyo (JP); Akito Yamabe, Tokyo (JP); Tsuyoshi Koriyama, Tokyo (JP)

(73) Assignee: Nippon Suisan Kaisha, Ltd. (JP)

( * ) Notice: Subject to any disclaimer, the term of this patent is extended or adjusted under 35 U.S.C. 154(b) by 184 days.

(21) Appl. No.: 12/682,687

(22) PCT Filed: Oct. 10, 2008

(86) PCT No.: PCT/JP2008/068420
§ 371 (c)(1),
(2), (4) Date: Apr. 12, 2010

(87) PCT Pub. No.: WO2009/048122
PCT Pub. Date: Apr. 16, 2009

(65) Prior Publication Data
US 2010/0217021 A1    Aug. 26, 2010

(30) Foreign Application Priority Data
Oct. 12, 2007    (JP) .................... 2007-267102

(51) Int. Cl.
*C11B 3/00*    (2006.01)
*C11B 3/02*    (2006.01)
*C11B 3/10*    (2006.01)
*A61K 31/20*   (2006.01)

(52) U.S. Cl. ............ 554/175; 554/8; 554/124; 554/141; 554/174; 554/230; 514/861; 514/558; 514/18.6

(58) Field of Classification Search ............ 554/8, 124, 554/141, 174, 175, 230; 514/18.6, 558, 861
See application file for complete search history.

(56) References Cited

U.S. PATENT DOCUMENTS
6,623,604 B1 *    9/2003    Elsasser et al. ................. 203/46

FOREIGN PATENT DOCUMENTS
| EP | 0108571 A2 | 5/1984 |
| JP | 1-53242 B2 | 11/1989 |
| JP | 5-117686 A | 5/1993 |
| JP | 11-100353 A | 4/1999 |

OTHER PUBLICATIONS

Yoshiyuki Hayashi et al., "Orange Roughy Oyobi Dory Oil no Seisei to sono Oyo", Dai 36 Kai Abstracts of the Meeting on Oil Chemistry, 1997 Nen, p. 24, with English translation.
Staoshi Yamanouchi et al., "Kaiyosei Wax Genryo no Tokucho to Hito Hifu eno Koka", Fragrance Journal, 2008 Nen 8 Gatsu, 36(7), pp. 83 to 87, with English translation.
International Search Report for PCT/JP2008/068420 mailed Nov. 4, 2008 with English translation.
Yushi, Yuryo Handbook, 1st edition 1st print, Kabushiki Kaisha Saiwai Shobo, 1988 Nen, p. 20, with English translation.
European Search Report for Application No./Patent No. 08838063.9-2114/2196523 dated Mar. 17, 2011.
Hui Y H et al.. "A Primer on Oils Processing Technology", Jan. 1, 1996, Bailey's Industrial Oil and Fat Products. Edible Oil and Fat Products: Processing Technology, John Wiley & Sons, Inc., New York, p. 1-60.

\* cited by examiner

*Primary Examiner* — Yate K Cutliff
(74) *Attorney, Agent, or Firm* — Cantor Colburn LLP

(57) ABSTRACT

An object of the present invention is to provide a more simplified and more efficient process for producing a highly purified orange roughy oil having high storage stability. The present invention provides a process for producing a highly purified orange roughy oil substantially free of a polyunsaturated fatty acid ester having 4 to 6 double bonds, and having a saponification value of 98 to 113 and an iodine value of 73 to 89, comprising washing with an alkaline aqueous solution to remove a free fatty acid; hydrogenating with a catalyst to reduce a polyunsaturated fatty acid ester; and purifying by treatment with an adsorbent.

9 Claims, No Drawings

PROCESS FOR PRODUCING HIGHLY PURIFIED ORANGE ROUGHY OIL

This is a U.S. national stage application of International Application No. PCT/JP2008/068420, filed on 10 Oct. 2008. Priority under 35 U.S.C. §119(a) and 35 U.S.C. §365(b) is claimed from Japanese Application No. JP2007-267102, filed 12 Oct. 2007, the disclosure of which is also incorporated herein by reference.

TECHNICAL FIELD

The present invention relates to a process for producing a highly purified orange roughy oil substantially free of a polyunsaturated fatty acid ester having 4 to 6 double bonds.

BACKGROUND ART

Orange roughy oils are oils extracted from *Hoplostethus atlanticus* (common name: orange roughy), *Hoplostethus mediterraneus*, *Hoplostethus gilchristi*, and *Hoplostethus intermedius*, all of which are bathybic Trachichthyidae fish having a large fat content, and contain a large amount of unsaturated aliphatic alcohol esters of unsaturated fatty acids. Orange roughy oils have less stickiness and a lightweight, smooth texture. There are standards set for ingredients of quasi-drugs of orange roughy oils that are obtained from *Hoplostethus atlanticus* (orange roughy) (Non-patent Citation 1).

However, traces of the distinctive fish oil smell of orange roughy oil remain even after deodorization treatment (Non-patent Citation 1). Since orange roughy oils contain traces of polyunsaturated fatty acids such as eicosapentaenoic acid and docosahexaenoic acid, the storage stability is low, and the fishy smell becomes stronger with time. These characteristics have been obstacles to use of orange roughy oils as an ingredient of cosmetic products and the like.

There are several reports on studies of using orange roughy oils as an ingredient of cosmetic products. Orange roughy oils were hydrogenated, but the hydrogenation products were in the form of a solid at room temperature and had significantly changed physical properties (Patent Citation 1). There is a report on a process for the production of purified orange roughy oils that retain monounsaturated fatty acid ester and from which only polyunsaturated fatty acid esters, which cause a fishy smell, are removed (Patent Citation 2). In this process, hydrogenation is carried out to a small degree so that only multivalent unsaturated bonds are hydrogenated, and this is followed by treatment with lipase to remove triglyceride components containing a large amount of polyunsaturated fatty acids. However, the resulting purified orange roughy oils do not meet the Japanese Standards of Quasi-drug Ingredients in a saponification value thereof and the like, and they are not usable as a base of external preparations or cosmetic products.

Patent Citation 1: JP H01-53242 B
Patent Citation 2: JP H05-117686 A
Non-patent Citation 1: Japanese Standards of Quasi-drug Ingredients 2006, Yakuji Nippo Limited, published in June 2006, pages 617-618

DISCLOSURE OF THE INVENTION

Problem to be Solved by the Invention

An object of the present invention is to provide a more simplified and more efficient process for producing a highly purified orange roughy oil having high storage stability.

Means for Solving the Problem

The present inventors conducted studies relating to various aspects of methods for the purification of orange roughy oils. Consequently, the inventors found that a highly purified orange roughy oil having high storage stability could be produced by a more simplified process, and then the present invention was completed.

In an aspect of the present invention, there is provided a process for producing a highly purified orange roughy oil comprising: washing with an alkaline aqueous solution to remove a free fatty acid, hydrogenating with a catalyst to reduce a polyunsaturated fatty acid ester, and purifying by treatment with an adsorbent; wherein the highly purified orange roughy oil is substantially free of a polyunsaturated fatty acid ester having 4 to 6 double bonds, and having a saponification value of 98 to 113 and an iodine value of 73 to 89.

In another aspect of the present invention, there is provided a highly purified orange roughy oil that can be produced by the process described above.

In a further aspect of the present invention, there is provided a cosmetic composition comprising the foregoing highly purified orange roughy oil, a moisturizing agent comprising the highly purified orange roughy oil described above, or a base for an external pharmaceutical composition comprising the highly purified orange roughy oil described above.

Advantages of the Invention

The present invention enables production of a highly purified orange roughy oil by a more simplified and more efficient process. A highly purified orange roughy oil produced by the process of the present invention has the original physical properties of orange roughy oil, which are derived from unsaturated alcohol esters of unsaturated fatty acids, meets the Japanese Standards of Quasi-drug Ingredients, and has excellent storage stability compared with that of conventional products.

Embodiment of the Invention

In the present invention, an orange roughy oil extracted from Trachichthyidae fish by a common method may be used as a raw material. For example, an orange roughy oil may be obtained by a method in which skins, subcutaneous fat, heads, and the like of *Hoplostethus japonicus* are boiled in water and surfacing oil is recovered and dehydrated.

A polyunsaturated fatty acid (PUFA) is a fatty acid having 16 or more carbon atoms and 3 or more double bonds. Examples of well-known PUFA include arachidonic acid (20 carbon atoms, 4 double bonds), eicosapentaenoic acid (EPA, 20 carbon atoms, 5 double bonds), docosapentaenoic acid (22 carbon atoms, 5 double bonds), docosahexaenoic acid (DHA, 22 carbon atoms, 6 double bonds), and linolenic acid (18 carbon atoms, 3 double bonds). Among these PUFA, those that are oxidized with time during storage and cause a fishy smell are polyunsaturated fatty acids having 4 to 6 double bonds, especially arachidonic acid, eicosapentaenoic acid, docosapentaenoic acid, and docosahexaenoic acid contained in an orange roughy oil. A highly purified orange roughy oil produced by the present invention is characterized in containing no polyunsaturated fatty acid having 4 to 6 double bonds as a constituent fatty acid and having high storage stability.

As used herein, the term "iodine value" refers to an amount by weight (g) of iodine that can be reacted with 100 g of fat and oil, and denotes a degree of unsaturation of the fat and oil.

The term "saponification value" refers to an amount by weight (mg) of potassium hydroxide required to saponify 1 g of fat and oil, and it reflects a type and a proportion of a higher fatty acid constituting the fat and oil. An acid value (AV) is an amount by weight (mg) of potassium hydroxide required to neutralize free fatty acids contained in 1 g of fat and oil, and denotes an amount of free fatty acids in the fat and oil. A peroxide value (POV) is an amount by weight (mg) of iodine liberated from potassium iodide by peroxides contained in 1 kg of fat and oil, and denotes an amount of lipid peroxide in the fat and oil.

The step of washing an orange roughy oil with an alkaline aqueous solution to remove free fatty acids may be carried out by any method known to a skilled person in the art. Examples of alkaline aqueous solutions that may be used therein include an aqueous solution of an alkali metal hydroxide, such as an aqueous solution of sodium hydroxide or potassium hydroxide. A concentration of an aqueous solution is appropriately adjusted based on a degree of acidity (acid value) of orange roughy oil to be washed. Preferably, the washed orange roughy oil has an acid value (mg KOH/g) of less than 1.0, especially preferably less than 0.5.

To remove nitrogenous substances and gum substances contained in orange roughy oil, the orange roughy oil may be washed with an aqueous solution of phosphoric acid or citric acid prior to washing with an alkaline aqueous solution. For example, an aqueous solution comprising 0.01% to 1% by weight of phosphoric acid with respect to the orange roughy oil (crude oil) may be used as an acid aqueous solution.

After washing with an acid aqueous solution and an alkaline aqueous solution, the orange roughy oil may be subjected to decolorization treatment with an adsorbent so that a catalyst to be used in selective hydrogenation reaction described below can fully exhibit catalytic effects. The decolorization treatment removes most of the distinctive color of orange roughy oil, and adsorbs substances having adverse effects on a catalyst (catalyst poison). Thus, the decolorization treatment is effective from an economical point of view and for process stabilization. An adsorbent to be used in the decolorization treatment is not particularly limited, but any adsorbent for use in purification of oils can be used. Examples of adsorbents that may be used include activated carbon, activated clay, diatomaceous earth, silica gel, alumina, zeolite, and molecular sieves. The treatment with an adsorbent is carried out by, for example, a method in which an adsorbent is added into oil and thereafter removed by filtration.

A catalyst that may be used in the step of hydrogenation to reduce polyunsaturated fatty acids includes a catalyst that preferentially acts on polyunsaturated fatty acid esters having 4 to 6 double bonds as a substrate and a catalyst that selectively hydrogenates polyunsaturated fatty acid esters while retaining unsaturated fatty acid ester having one or two double bonds. Examples of such a catalyst include a copper-chromium oxide catalyst (Adkins catalyst). Manganese oxide ($Mn_2O_3$) and/or barium oxide (BaO) may be contained as a co-catalyst. The catalysts may be in the form of granules or powder, or may be a molded article such as a cylindrical form. For example, the catalysts may be in the form of powder with an average particle size of about 0.1 μm to about 100 μm, preferably about 1 μm to about 30 μm.

In view of selectivity of reaction and operational efficiency, for example, the hydrogenation is carried out under a condition using a catalyst in an amount of 0.5% to 5% by weight, preferably 1% to 3% by weight, with respect to oil used as a substrate, and at a hydrogen pressure of 1.0 kgf/cm$^2$ to 5.0 kgf/cm$^2$, preferably 1.1 kgf/cm$^2$ to 1.5 kgf/cm$^2$, based on an absolute pressure. The hydrogenation is carried out at a reaction temperature of, for example, 80° C. to 250° C., preferably 120° C. to 200° C. A reaction time for selective hydrogenation of polyunsaturated fatty acid esters having 4 to 6 double bonds can be appropriately determined by a person skilled in the art based on reaction conditions. The reaction time may be, for example, about 2 hours to about 10 hours.

An adsorbent to be used in the treatment with an adsorbent after the hydrogenation is not particularly limited, but any adsorbent for use in purification of oils may be used. Examples of adsorbents that can be used include activated carbon, activated clay, diatomaceous earth, silica gel, alumina, zeolite, and molecular sieves. In the treatment with an adsorbent, for example a column filled with an adsorbent may be used, and a solvent such as hexane may be used. The treatment with an adsorbent after the hydrogenation removes triglycerides as well as distinctive smells remaining in the orange roughy oil. In the process of the present invention, the treatment with an adsorbent may be carried out once, twice, or more.

Generally, the steps of deoxidation, hydrogenation, and purification by treatment with an adsorbent in the present invention are preferably carried out in this order, but the order of the steps may be changed depending on a situation, or another step such as a decolorization step may be added as necessary.

A highly purified orange roughy oil produced by the present invention has a saponification value (mg KOH/g) of 98 to 113 and an iodine value (g I$^2$/100 g) of 73 to 89, and its physical properties such as a viscosity and a melting point are almost the same as those of conventionally-used orange roughy oils. Thus, a highly purified orange roughy oil produced by the present invention has a characteristic of a conventional orange roughy oil, namely a lightweight, smooth texture. Further, a highly purified orange roughy oil produced by the present invention does not have the distinctive smell of orange roughy oil and is substantially free of polyunsaturated fatty acid esters having 4 to 6 double bonds. Thus, it has excellent storage stability, compared with conventionally-used orange roughy oils (e.g., orange roughy oils described in the drugs the Japanese Standards of Quasi-drug Ingredients).

As stated above, a highly purified orange roughy oil obtained by the process of the present invention meets the standards of quasi-drug ingredients of orange roughy oils, retains the original properties of orange roughy oil and, furthermore, does not contain polyunsaturated fatty acids having low oxidation stability, resulting in excellent stability. Therefore, a highly purified orange roughy oil obtained by the process of the present invention can be used extensively as base materials of cosmetic products and external pharmaceutical products. Furthermore, a highly purified orange roughy oil produced by the process of the present invention is also excellent in skin safety. Namely, it does not exhibit any irritability or the like not only to healthy skins but also to skins in a pathological condition such as atopy, and is thus safe to use. Since wax esters have moisturizing effects to reduce drying of skins, a highly purified orange roughy oil can be used not only as a base material but also as a moisturizing agent.

As shown in the Examples, no irritability was observed in primary human skin irritation tests using 48-hour closed patch testing regarding a highly purified orange roughy oil obtained by a process of the present invention. Furthermore, no side effect was observed in tests applying to mild atopic dermatitis patients for 6 weeks. Accordingly, a highly purified orange roughy oil of the present invention can be used in, for example, external moisturizing agents for the therapy or prophylaxis of inflammatory skin diseases, i.e. external moisturizing agents for the therapy or prophylaxis of inflammatory skin diseases comprising a highly purified orange roughy oil substantially free of polyunsaturated fatty acid esters having 4 to 6 double bonds.

Inflammatory skin diseases to which the external moisturizing agents are applicable are not particularly limited. Examples include inflammatory diseases associated with symptoms such as dryness, desquamation, erythema, and pruritus of skins of a face, a torso, and extremities. The external moisturizing agents are especially applicable to atopic dermatitis.

The external moisturizing agents stated above may contain a drug that is conventionally used to treat inflammatory skin diseases, especially atopic skin diseases; for example, one or more components selected from steroidal anti-inflammatory drugs, non-steroidal anti-inflammatory drugs, antiallergic agents, immunosuppressive drugs, and the like. Examples of steroidal anti-inflammatory drugs include hydrocortisone acetate, hydrocortisone butyrate, prednisolone, alclometasone propionate, dexamethazone propionate, betamethasone butyrate propionate, fluocinonide, and hydrocortisone butyrate propionate. Examples of non-steroidal anti-inflammatory drugs include ibuprofen. Examples of antiallergic agents include diphenhydramine hydrochloride, clemastine fumarate, chlorpheniramine maleate, and azelastine hydrochloride. Examples of immunosuppressive drugs include tacrolimus.

The highly purified orange roughy oil of the present invention may be used as a base material of external preparations in the form of an ointment, a cream, or the like for direct application to a local skin surface. Examples of such external preparations include lotions, oil ointments, emulsion ointments (cream), water-soluble ointments, and sprays.

As necessary, the external preparations may contain a base material, an absorption promoting agent, a thickening agent, an emulsifying agent, a coloring agent, a perfuming agent, an antioxidant agent, a stabilizing agent, a germicidal agent, an antiseptic agent, and the like that are generally used in an external preparation.

The following non-limiting Examples illustrate the present invention in detail.

EXAMPLES

Production of Highly Purified Orange Roughy Oil
1. Deacidification and Decolorization Steps A phosphoric acid aqueous solution (100 kg) containing phosphoric acid (0.5 kg) was added to an orange roughy crude oil (1000 kg Orange Roughy Crude Oil purchased from SEALORD, New Zealand; acid value: 3.4, iodine value: 90, and saponification value: 111), and the mixture was stirred at 70° C. for 0.5 hours, and then an aqueous layer was separated. A sodium hydroxide aqueous solution (total 50 kg, including 2.8 kg of sodium hydroxide) was added to the oil layer, and the mixture was stirred at 70° C. for 10 minutes and then kept still, followed by separation of an aqueous layer. The oil layer was washed with water (300 kg) and an aqueous layer was separated. Water (300 kg) was further added for washing and an aqueous layer was separated. The oil layer was dried by heating and stirring under reduced pressure (20 torr) at 80° C. to 110° C. for 30 minutes. Thereafter, activated clay (10 kg) was added, and the mixture was stirred for 30 minutes with heating (90° C.). The activated clay was removed by filtration to obtain a purified orange roughy oil (945 kg). The resulting orange roughy oil had an acid value of 0.35, an iodine value of 89, and a saponification value of 109.

2. Hydrogenation Step

A copper-chromium oxide catalyst (30 g, N203SD, JGC Corporation) was added to the purified orange roughy oil (2 kg) in an autoclave, and the mixture was dried by heating and stirring under reduced pressure (20 torr) at 110° C. for 30 minutes. Then, the mixture was heated to 150° C., and hydrogen (10 g) was injected into the autoclave. The mixture was stirred for 3 hours while the reaction temperature was adjusted to 150° C. to 200° C. and the inner pressure of the vessel to 1.3 kgf/cm$^2$ to 1.5 kgf/cm$^2$. Thereafter, the reaction mixture was cooled to about 70° C., and the catalyst was removed by filtration to obtain a hydrogenated orange roughy oil (1.9 kg).

The changes in composition of fatty acid and alcohol portions of the orange roughy oil between before and after the hydrogenation are shown in Table 1. A saponified portion in an aqueous layer obtained by saponification of the resulting oil was acidified, and the resulting fatty acid fraction was collected from the surface of the aqueous layer. Analysis of the fatty acid portions was conducted by gas chromatography on a sample obtained by conversing the fatty acid fraction to methyl ester using a conventional method. Analysis of alcohol portions was conducted by gas chromatography on the unsaponifiable fraction that was obtained after the saponification treatment.

TABLE 1

| Number of carbon atoms of fatty acid ester:number of double bonds | Before hydrogenation | | After hydrogenation | |
|---|---|---|---|---|
| | Fatty Acid Portion | Alcohol Portion | Fatty Acid Portion | Alcohol Portion |
| C 14:0 | 1.5 | 2.7 | 1.3 | 2.7 |
| C 14:1 | 0.3 | | 0.3 | |
| C 16:0 | 2.5 | 22.6 | 1.5 | 22.5 |
| C 16:1 | 12.5 | 2.7 | 11.7 | 2.7 |
| C 18:0 | 0.8 | 6.0 | 0.8 | 5.6 |
| C 18:1 | 55.2 | 18.2 | 55.0 | 17.2 |
| C 18:2 | 1.0 | | 0.9 | |
| C 20:0 | | 0.6 | | 0.6 |
| C 20:1 | 14.5 | 24.2 | 16.8 | 25.0 |
| C 20:4 | 0.8 | | | |
| C 20:5 | 1.1 | | | |
| C 22:0 | | 0.2 | | 0.3 |
| C 22:1 | 5.3 | 15.0 | 6.4 | 15.7 |
| C 22:5 | 0.2 | | | |
| C 22:6 | 1.1 | | | |
| C 24:1 | | 3.1 | | 2.9 |

The compositions of alcohol and fatty acid were analyzed by the following method.

The composition of alcohol was analyzed in accordance with the JOCS Standard Methods for the Analysis of Fats, Oils and Related Materials (edited by the Japan Oil Chemists' Society, 2003), "2,4,8$_{-1996}$ Unsaponifiable matter." A solution of potassium hydroxide (1 mol) in ethanol (90%) was added to a sample (about 5 g) in a vessel equipped with a condenser, and the mixture was heated to reflux for 1 hour. Water (150 ml) was added and the mixture was cooled to a room temperature, followed by extraction with diethyl ether (100 ml) and then extraction with diethyl ether (50 ml) twice. The combined extract was washed with water (30 ml) repeatedly until the wash liquid became neutral. The diethyl ether was distilled off, and the resulting mixed alcohol was diluted with hexane to an appropriate concentration and then injected into gas chromatography of the following operational conditions.

To analyze the fatty acid composition, mixed fatty acids that were obtained at the preparation of unsaponifiable matters were converted into methyl esters in accordance with, "2,4,1,2-1996 Methyl esterification method" (trifluoroboron methanol method) in the JOCS Standard Methods. Hydrochloric acid (2 mol, 30 ml) was added to a lower layer (water-ethanol layer) that was obtained after diethyl ether extraction to be acidic, followed by extraction with diethyl ether (100 ml). The extract was washed with water (50 ml) until the wash liquid became neutral. The dimethyl ether was distilled off to obtain a mixed fatty acid. To the resulting mixed fatty acid (about 20 mg), a solution of boron trifluoride in methanol (14%, 1 ml) was added, and the mixture was heated to reflux for 2 minutes in a vessel equipped with a condenser. Thereafter, hexane (5 ml) was added, and the mixture was further refluxed for 1 minute. After cooling, a saturated sodium chloride solution (30 ml) was added, and the mixture was shaken and thereafter kept still. Then, a hexane solution of an upper layer was injected into gas chromatography of the following operational conditions.

Gas Chromatography Operational Conditions:

Capillary column. DB-WAX (J&W Scientific), Fused Silica Capillary Column, 0.25 mm I.D.×30 m, 0.25 μm film thickness Carrier gas: helium Detector: 250° C., FID Inlet: 250° C., split ratio=100:1

Column temperature: 180° C.→3° C./min→230° C. (15 min)

Apparatus: Hewlett Packard 6890

The orange roughy oil before the hydrogenation contained arachidonic acid (C20:4), eicosapentaenoic acid (C20:5), docosapentaenoic acid (C22:5), and docosahexaenoic acid (C22:6), but it was confirmed that esters containing these polyunsaturated fatty acids as a fatty acid portion were completely eliminated by the hydrogenation. The hydrogenated orange roughy oil had an acid value of 0.1, an iodine value of 79, and a saponification value of 107.

3. Purification Step

Hexane (300 ml) was added to the hydrogenated orange roughy oil (100 g), and the resulting solution was passed through a column that was filled with an adsorbent (100 g of activated clay). Thereafter, the column was washed with hexane (100 ml). The hexane was distilled off under reduced pressure from the combined hexane solution, and the resulting oil was steam distilled (10 torr to 20 torr, 180° C. to 190° C.) to obtain a highly purified orange roughy oil (85 g). The highly purified orange roughy oil had an acid value of 0.05, an iodine value of 79, and a saponification value of 104.

The resulting highly purified orange roughy oil was charged into transparent glass bottles and left without a lid at room temperature or 50° C. Peroxide values and the results of sensory evaluation are shown in Tables 2 and 3, respectively.

TABLE 2

Results of storage test

| Number of days of storage | 0 | 23 | 35 | 52 | 61 | 89 |
|---|---|---|---|---|---|---|
| Stored at room temperature | 0.1 | 0.5 | 0.8 | 1.2 | 17.9 | 90.6 |
| Stored at 50° C. | 0.1 | 2.8 | 105.2 | — | — | — |

(change in POV during the storage, POV unit: meq/kg)

TABLE 3

Results of storage test

| Number of days of storage | 0 | 23 | 35 | 52 | 61 | 89 |
|---|---|---|---|---|---|---|
| Stored at room temperature | 0.25 | 0.5 | 1.0 | 1.0 | 1.25 | 1.75 |
| Stored at 50° C. | 0.25 | 1.0 | 1.75 | — | — | — |

(intensity of smell during storage, 0: no smell was sensed, 1: very slight smell was sensed, 2: slight smell was sensed, 3: smell was sensed, 4: strong smell was sensed, 5: extremely strong smell was sensed; average points of four persons)

It was confirmed from the results that the highly purified orange roughy oil could be stably stored for 23 days in the case of storage at 50° C., and for 52 days in the case of storage at a room temperature in light of the increases in POV. With regard to smell, all the evaluated samples were assessed as 2 or below.

Test Example 1

To confirm skin safety of an orange roughy oil of the present invention that was produced by the process stated above, "primary human skin irritation tests by 48-hour closed patch testing" were conducted.

Test sample: Orange roughy oil of the present invention and, as a control, distilled water for injection or white vaseline Method: Among candidates who understood the purpose of the tests, 23 women at an age of 18 or older were selected as subjects. A Firm Chamber (EPITEST, Finland) or Scanpor tape (NORGESPLASTER, Norway) was used as a patch test unit, and an orange roughy oil of the present invention and a control were applied to backs (paravertebral part) of the subjects for 48 hours. Specialists judged 30 to 60 minutes after the removal of the unit (48 hours after the application) and 72 hours after the application in accordance with the judgment standards shown in Table 4.

TABLE 4

| Judgment Standards | Reaction |
|---|---|
| − | no reaction |
| ± | slight erythema |
| + | erythema |
| ++ | erythema + edema, papule |
| +++ | erythema + edema, papule + vesicle |
| ++++ | bulla |

Results: No primary skin irritation was observed in any of the cases of application of the orange roughy oil and application of the control.

Test Example 2

Utility and safety tests were conducted on the highly purified orange roughy oil by the following procedure. Japanese women at an age of 20 to 49 (twenties: 11 women, thirties: 7 women, forties: 4 women; average age 30.0) who had minor symptoms of atopic dermatitis on a face or answered in a questionnaire that they were conscious of dry, sensitive face skin were selected. The test sample was applied to an entire face and a designated forearm twice a day (morning and evening) after washing a face or taking a bath for 6 weeks. Skin observation and measurement were carried out before the use, after 3 weeks, and after 6 weeks. A doctor observed xerosis, scale, erythema, and pruritus in portions of an entire face to be examined, and evaluated the symptoms on a scale of 1 to 5 (1: none, 2: minor, 3: mild, 4: moderate, 5: severe), thereby recording findings in skin. The skin measurement was carried out with Skicon-EX200 by measuring five times a moisture content of a horny layer of portions in cheeks and forearms to which the test sample was applied and portions to which no test sample was applied, and an average of the results excluding the greatest value and the smallest value was employed. The skin observation and measurement were carried out after the women who had washed their face stayed in an environment-adjustable room that was maintained at a temperature of 21° C. (±2° C.) and a humidity of 45% (±5%) for at least 15 minutes to be naturalized to the environment.

1. Improvement Rate in Findings of Skin

Improvement rates were calculated from total symptom scores of the findings in skin on the first day of the test, on the day after 3 weeks, and on the day after 6 weeks, and evaluated on a scale of 1 to 5 (1: significantly relieved, 66%≦improvement rate≦100%, 2: moderately relieved, 33%≦improvement rate<66%, 3: slightly relieved, 0%<improvement rate<33%, 4: unchanged, improvement rate=0%, 5: worsened, improvement rate<0%). A mathematical formula for the calculation of the improvement rates and the test results are shown below.

[Mathematical formula 1]

$$\text{Improvement rate} = \frac{\text{Total score on the first day of the test} - \text{Total score on the day after 3 or 6 weeks}}{\text{Total score on the first day of the test}} \times 100(\%)$$

TABLE 5

| Symptom improvement rate judgment standards | After 3 weeks | After 6 weeks |
| --- | --- | --- |
| 1. Significantly relieved | 0 | 0 |
| 2. Moderately relieved | 4 | 15 |
| 3. Slightly relieved | 16 | 7 |
| 4. Unchanged | 1 | 0 |
| 5. Worsened | 1 | 0 |

Improvements in the symptoms were observed in 91% of the subjects on the day after 3 weeks, and in all cases on the day after 6 weeks.

2. Change in Moisture Content of Horny Layer of Forearm

A transition of moisture contents of horny layers of forearms (portions to which the test sample was applied, and portions to which no test sample was applied) on observation days in the skin measurement is shown below.

TABLE 6

|  | Before the use | After 3 weeks | After 6 weeks |
| --- | --- | --- | --- |
| Portions to which the test sample was applied | | | |
| Average | 50.08 | 80.06 | 86.24 |
| SD | 17.70 | 30.95 | 42.95 |
| Portions to which no test sample was applied | | | |
| Average | 48.82 | 55.38 | 57.58 |
| SD | 14.71 | 18.20 | 21.14 |

In comparisons of the first day of the test with the day after 3 weeks and the day after 6 weeks, a statistically significant increase was observed in the moisture content of the portions to which the test sample was applied.

3. Change in Moisture Content of Horny Layer of Face

A transition of moisture contents of horny layers of faces on observation days in the skin measurement is shown below.

TABLE 7

|  | First day of the test | After 3 weeks | After 6 weeks |
| --- | --- | --- | --- |
| Average | 152.29 | 179.35 | 192.97 |
| SD | 63.95 | 67.42 | 66.35 |

In comparisons of the first day of the test with the day after 3 weeks and the day after 6 weeks, a statistically significant increase was observed.

4. Evaluation of Safety

There was no case of cessation or dropout during the 6-week tests. Further, no side effect was observed, and the safety of the test sample was confirmed.

The invention claimed is:

1. A process for producing a highly purified orange roughy oil comprising:
   (i) washing with an alkaline aqueous solution to remove a free fatty acid,
   (ii) decolorizing by treatment with an adsorbent,
   (iii) hydrogenating with a catalyst to reduce a polyunsaturated fatty acid ester having 4 to 6 double bonds, and
   (iv) purifying by treatment with an adsorbent;
   wherein steps (i) to (iv) are carried out in the given order; and
   wherein the highly purified orange roughy oil is substantially free of a polyunsaturated fatty acid ester having 4 to 6 double bonds, and has a saponification value of 98 to 113 and an iodine value of 73 to 89.

2. The process according to claim 1, wherein the catalyst is a copper-chromium oxide catalyst.

3. The process according to claim 1, wherein the treatment with the adsorbent is treatment with an activated clay and/or an activated carbon.

4. The process according to claim 1, wherein the hydrogenation is carried out at a hydrogen pressure of 1.0 kgf/cm$^2$ to 5.0 kgf/cm$^2$.

5. A highly purified orange roughy oil with 23 days storage stability at 50° C. and/or 52 days storage stability at room temperature, wherein the highly purified oil is substantially free of a polyunsaturated fatty acid having 4 to 6 double bonds, and having a saponification value of 98 to 113 and an iodine value of 73 to 89.

6. A cosmetic composition comprising the highly purified orange roughy oil according to claim 5.

7. A moisturizing agent comprising the highly purified orange roughy oil according to claim 5.

8. A base material for an external pharmaceutical composition comprising the highly purified orange roughy oil according to claim 5.

9. A method for treating mild atopic dermatitis comprising applying to human skin an effective amount of the moisturizing agent of claim 7.

* * * * *